(12) United States Patent
Bak et al.

(10) Patent No.: US 6,965,064 B2
(45) Date of Patent: Nov. 15, 2005

(54) *GUZMANIA* PLANT NAMED 'SWITCH'

(76) Inventors: Elly Bak, Aalsmeerderweg 682, Rijsenhout 1435 ER (NL); Nicolaas D. M. Steur, Skarpetweg 7, Oude Niedorp 1734 JL (NL)

( * ) Notice: Subject to any disclaimer, the term of this patent is extended or adjusted under 35 U.S.C. 154(b) by 0 days.

(21) Appl. No.: 10/372,933

(22) Filed: Feb. 26, 2003

(65) Prior Publication Data
US 2004/0168233 P1 Aug. 26, 2004

(51) Int. Cl.$^7$ .............. A01H 5/00; A01H 1/00; A01H 1/02
(52) U.S. Cl. ............... 800/323; 800/298; 800/260
(58) Field of Search .................. 800/323, 260, 800/298

*Primary Examiner*—Kent Bell
(74) *Attorney, Agent, or Firm*—Richard C. Peet

(57) ABSTRACT

*Guzmania* cultivar 'Switch' is solid, tenable, small-sized and long lasting with a compound-shaped purple-red inflorescence.

4 Claims, 2 Drawing Sheets

(2 of 2 Drawing Sheet(s) Filed in Color)

GUZMANIA PLANT NAMED 'SWITCH'

FIELD OF THE INVENTION

The present invention relates to a new, distinct and stable plant of *Guzmania* hybrid, hereinafter referred to as 'Switch'. The present invention relates to seeds which are *Guzmania* cultivar 'Switch', as well as plants and plant parts produced from these seeds which have all the morphological and physiological characteristics of the *Guzmania* cultivar 'Switch'. The present invention also relates to methods for producing these seeds and plants. Furthermore, the present invention relates to a method of producing progeny *Guzmania* plants by crossing *Guzmania* cultivar 'Switch', as the male or female parent, with another *Guzmania* plant and selecting progeny.

BACKGROUND OF THE INVENTION

The new cultivar is a hybrid *Guzmania*. The male or pollen parent was a selection of *Guzmania wittmacki* and the female or seed parent was a selection of *Guzmania lingulata*. *Guzmania* is a member of the Bromeliaceae family. *Guzmania* is predominantly epiphytic with a few terrestrial species and is native to the tropics. For the most part, species vary in diameter from 7 or 8 inches to 3 or 4 feet and have rosettes of glossy, smooth-edged leaves.

Floral bracts of *Guzmania* frequently have brilliant colors and may last for many months. The range of colors for *Guzmania* is generally from yellow through orange but may also include flame red and red-purple. White or yellow, tubular, three-petalled flowers may also appear on a stem or within the leaf rosette but are usually short-lived.

*Guzmania* may be advantageously grown as pot plants for greenhouse or home use. Typically, the plants are shaded from direct sunlight. During the spring to autumn period, the central vase-like part of the leaf rosette is normally filled with water.

*Guzmania* is native to tropical America. Leaves of *Guzmania* are usually formed as basal rosettes which are stiff and entire and in several vertical ranks. *Guzmania* plants have terminal spikes or panicles which are often bracted with petals united in a tube about as long as the calyx. The ovary is superior and the seeds plumose.

Asexual propagation of *Guzmania* is frequently done through the use of tissue culture practices. Propagation can also be from offshoots which can be detached from the mother plant and grown in an appropriate soil or bark mixture.

Methods for cultivation and crossing of *Guzmania* are well known. For a detailed discussion, reference is made to the following publications, which are incorporated herein by reference: Benzing, David H., THE BIOLOGY OF THE BROMELIADS, Mad River Press, Inc., Eureka (1980); Zimmer, Karl, BROMELIEN, Verlag Paul Parey, Berlin (1986); and Rauh, Werner, BROMELIEN, Verlag Eugen Ulmer, Stuttgart (1981).

A *Guzmania* inbred is produced by brother/sister crossing over several generations to produce a genetically homozygous plant selection. A hybrid cultivar is produced by crossing two genetically distinct inbred lines, collecting seeds produced by the cross, and germinating seeds so-produced to make hybrid plants. The hybrid seeds and plants produced by this method are uniform with respect to their morphological and physiological characteristics.

A need exists for a greater variety of *Guzmania* cultivars with attractive ornamental features. Additionally, a need exists for additional *Guzmania* hybrid cultivars that can be easily propagated by seed. The new cultivar was developed through a controlled breeding program and exhibits unique, desirable and stable characteristics.

SUMMARY OF THE INVENTION

The instant invention provides *Guzmania* plant selections that are solid, tenable, small-sized and long-lasting. The instant invention also provides *Guzmania* plant selections with a compound-shaped purple-red inflorescence.

These and other objectives have been achieved in accordance with the present invention which provides a new cultivar 'Switch' that is a product of a planned breeding program undertaken by the inventors in Assendelft, The Netherlands, in 1996. The male or pollen parent was a selection of *Guzmania wittmacki* identified by Code No. 93517036. The female or seed parent was a selection of *Guzmania lingulata* identified by Code No. 93517146.

Both parents have a sufficient degree of homozygosity such that the progeny of the cross are genetically and phenotypically uniform. The cultivar 'Switch' therefore can be produced by sexual reproduction by crossing 93517036× 93517146 to produce a population of progeny plants, each of which has the combination of characteristics as herein disclosed for the new cultivar.

Seeds which are cultivar 'Switch' are produced by crossing 93517036×93517146 and are deposited with the American Type Culture Collection, 10801 University Boulevard, Manassas, Va. 20110-2209 (ATCC Patent Deposit Designation No. PTA-4824). 2500 seeds were deposited with the ATCC on Nov. 26, 2002.

OBJECTS OF THE INVENTION

This invention relates to seeds which produce *Guzmania* cultivar 'Switch'. This invention also relates to *Guzmania* plants, and parts thereof, having all the physiological and morphological characteristics of *Guzmania* cultivar 'Switch'. This invention relates to a plant produced from seeds which are *Guzmania* cultivar 'Switch'. This invention also relates to plant parts, such as pollen, seeds or inflorescence produced by *Guzmania* cultivar 'Switch'.

This invention relates to a method of producing seed which are *Guzmania* cultivar 'Switch', by crossing *Guzmania wittmacki* selection 93517036 as the male parent with *Guzmania lingulata* selection 93517146 as the female parent and the reciprocate cross with 93517146 as the female parent and 93517036 as the male parent and harvesting seeds produced from said crosses.

This invention also relates to a method of producing plants having all the physiological and morphological characteristics of the *Guzmania* cultivar 'Switch' comprising the steps of (a) crossing *Guzmania wittmacki* selection 93517036 as the male parent with *Guzmania lingulata* selection 93517146 as the female parent; (b) harvesting seeds produced from said cross; and (c) producing plants from said harvested seeds.

The invention also relates to producing progeny plants from the cross of *Guzmania* cultivar 'Switch', as the male or female parent, with another *Guzmania* plant, and selecting progeny plants from this cross.

BRIEF DESCRIPTION OF THE DRAWINGS

The file contains at least two drawings executed in color. Copies of this patent with the color drawings will be provided by the Patent and Trademark Office upon request and payment of the necessary fee.

The first photographic drawing shows a whole plant, side view of the inflorescence and foliage of 'Switch', with colors being as true as possible with illustrations of this type.

Figure 1:
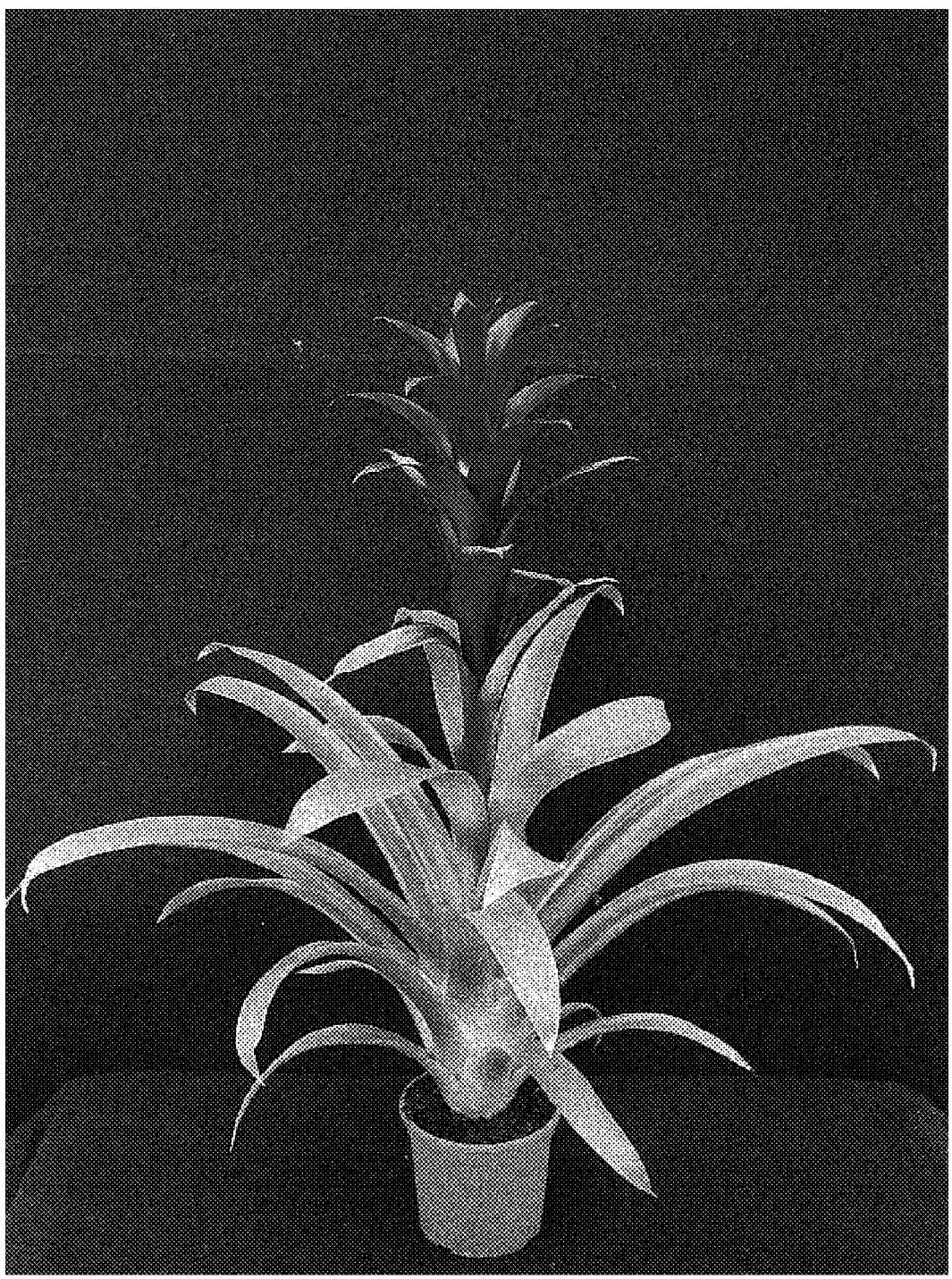
Figure 2:

The second photographic drawing shows a close up, side view of the inflorescence of 'Switch'.

DETAILED DESCRIPTION OF THE PREFERRED EMBODIMENTS

The present invention was created by the inventors, Elly Bak and Nicolaas D. M. Steur in 1993, and flowered for the first time in 1996 in Assendelft, The Netherlands.

This invention is directed to a *Guzmania* plant having all the morphological and physiological characteristics of the cultivar 'Switch' produced from seeds which are the product of the cross of *Guzmania wittmacki* selection 93517036 as the male parent with *Guzmania lingulata* selection 93517146 as the female parent. Both parents have a sufficient degree of homozygosity such that the progeny of the cross were, and continue to be, phenotypically uniform. The variety 'Switch' therefore can be produced by sexual reproduction by crossing 93517036×93517146 to produce a population of progeny plants each of which has the combination of characteristics as herein disclosed for the new cultivar.

The variety 'Switch' can also be produced by asexually reproducing progeny from the cross of 93517036×93517146 because the combination of characteristics as herein disclosed for the new cultivar 'Switch' are firmly fixed and are retained through successive generations of asexual reproduction. The selection comprising the new variety was chosen after commencement of flowering of the progeny in 1996 in Assendelft, The Netherlands. Sexual propagation has demonstrated that the combination of characteristics as herein disclosed for the new cultivar 'Switch', as observed in Assendelft, The Netherlands, are firmly fixed and are retained through successive generations of asexual reproduction.

'Switch' is particularly characterized by the following characteristics:
1. solid, tenable, small-sized growth habit in a funnel-form rosette measuring approximately 55 cm in height when flowering;
2. numerous leaves, each approximately 40 cm in length;
3. approximately 10 scape bracts and 10 primary bracts;
4. compound-shaped inflorescence;
5. purple-red primary bracts, RHS 185A; and
6. long-lasting habit.

'Switch' has not been tested under all available environmental conditions. The phenotype may vary with variations in environmental conditions such as temperature, light intensity, frequency of fertilization, composition of fertilizer, acetylene treatment, day length and humidity without, however, any change in the genotype of the new cultivar.

For example, substantial differences in plant height and diameter, and the number of leaves, can result depending on the size of the plant at the time flowering is induced by acetylene treatment. Since treatment with acetylene to induce flowering disrupts normal watering and fertilization regimens, acetylene treatment of relatively smaller plants adversely affects the growth of the plant.

The new cultivar flowers approximately 17 weeks after treatment with Acetylene.

The closest comparison cultivar is *Guzmania* 'Ostara' (unpatented). The most important difference between 'Switch' and 'Ostara' is the color of the inflorescence. 'Switch' has a purple-red inflorescence, while 'Ostara' has an orange-red inflorescence.

In the following description, color references are made to the Royal Horticultural Society Colour Chart (RHS). The following traits have been repeatedly observed and in combination distinguish 'Switch' as a new and distinct cultivar. The following observations, measurements and descriptions were taken of 'Switch' plants grown under Dutch greenhouse conditions in Assendelft, The Netherlands.

| PLANT: | |
| --- | --- |
| Form: | Funnel form rosette |
| Height: | Approximately 55 cm high (flowering) |
| Diameter: | Approximately 60 cm |
| Growth habit: | Stemless |
| FOLIAGE: | |
| Size: | Approximately 40 cm in length, 3–4 cm in width |
| Shape: | Lanceolate |
| Surface texture: | Smooth |
| Color: | Upperside: between RHS 147 A; underside: RHS 137 A (color can vary depending on environmental conditions) |
| Apex: | Acute |
| FLOWERS: | |
| Borne: | Erect stalks |
| Shape of inflorescence: | Compound |
| Size of the inflorescence: | Approximately 20 cm in length; approximately 23–25 cm in diameter |
| Individual petals: | Approximately 6 cm in length; .5 cm in width; color RHS 17 A |
| Number of flowers per inflorescence: | Approximately 80 |
| Lastingness of the inflorescence: | A full grown plant can produce an inflorescence containing approximately 80 flowers and can bloom anytime throughout the year beginning approximately 17 weeks after natural induction or induction with acetylene. Each flower blooms for one day and the total length of blooming of the whole inflorescence is 6 weeks. |
| BRACTS: | |
| Scape Bract: | Approximately 20 cm (lowest) to approximately 12 cm just below the primary bracts in length; approximate 3.5–4 cm in width; approximately 10 in number; lanceolate shape; smooth texture; margin entire; acute apex |
| Primary Bract: | Approximately 12 cm (lowest) to approximately 4 cm at the top in length; approximately 2.5–3.5 cm in width; approximately 10 in number; lanceolate shape; smooth texture; margin entire; acute apex; color RHS 185 A |
| Floral Bract: | Disposed within the inflorescence |

What is claimed is:

1. A *Guzmania* plant designated cultivar 'Switch' obtained from seed having American Type Culture Collection (ATCC) Patent Deposit Designation No. PTA-4824.

2. *Guzmania* seed having ATCC Patent Deposit Designation No. PTA-4824.

3. Plant parts obtained from the *Guzmania* plant of claim 1.

4. A method of producing *Guzmania* progeny plant comprising of the steps of (a) crossing *Guzmania* cultivar 'Switch' produced from seed accorded ATCC Patent Deposit Designation No. PTA-4824 as a male or female parent with another *Guzmania* plant and (b) selecting progeny.

* * * * *

UNITED STATES PATENT AND TRADEMARK OFFICE
CERTIFICATE OF CORRECTION

PATENT NO. : 6,965,064 B2
DATED : November 15, 2005
INVENTOR(S) : Elly Bak and Nicolaas D.M. Steur It is certified that error appears in the above-identified patent and that said Letters Patent is hereby corrected as shown below:

Title page,
Insert Item -- [73] Assignee, Corn.Bak. B.V., Assendelft, Netherlands --.

Signed and Sealed this

Fourteenth Day of February, 2006

JON W. DUDAS
*Director of the United States Patent and Trademark Office*

UNITED STATES PATENT AND TRADEMARK OFFICE
CERTIFICATE OF CORRECTION

PATENT NO. : 6,965,064 B2
APPLICATION NO. : 10/372933
DATED : November 15, 2005
INVENTOR(S) : Bak et al.

It is certified that error appears in the above-identified patent and that said Letters Patent is hereby corrected as shown below:

On the Title page,

[*] Notice: Subject to any disclaimer, the term of this patent is extended or adjusted under 35 USC 154(b) by (0) days Delete the phrase "by 0 days" and insert -- by 284 days--

Signed and Sealed this

Third Day of April, 2007

JON W. DUDAS
*Director of the United States Patent and Trademark Office*